United States Patent [19]

Bossert et al.

[11] 4,248,873

[45] Feb. 3, 1981

[54] NITRO-SUBSTITUTED 1,4-DIHYDROPYRIDINES, PROCESSES FOR THEIR PRODUCTION AND THEIR MEDICINAL USE

[75] Inventors: Friedrich Bossert; Gerhard Franckowiak; Arend Heise; Stanislav Kazda; Horst Meyer; Kurt Stoepel; Robertson Towart; Egbert Wehinger, all of Wuppertal, Fed. Rep. of Germany

[73] Assignee: Bayer Aktiengesellschaft, Leverkusen, Fed. Rep. of Germany

[21] Appl. No.: 958,239

[22] Filed: Nov. 6, 1978

[30] Foreign Application Priority Data

Nov. 26, 1977 [DE] Fed. Rep. of Germany ....... 2752820

[51] Int. Cl.³ ..................... A61K 31/44; C01D 211/84

[52] U.S. Cl. .................................... 424/256; 424/250; 424/251; 544/238; 544/333; 544/353; 544/405; 546/144; 546/167; 546/255; 546/256; 546/257; 546/258; 546/268; 546/270; 546/271; 546/273; 546/275; 546/276; 546/278; 546/279; 546/280; 546/281; 546/283; 546/284; 546/304; 546/307; 546/310; 546/312

[58] Field of Search ....................... 546/304, 307, 310; 424/256

[56] References Cited

U.S. PATENT DOCUMENTS 4,001,252 1/1977 Meyer et al. ........................ 546/307

*Primary Examiner*—Joseph Paul Brust

*Attorney, Agent, or Firm*—Sprung, Felfe, Horn, Lynch & Kramer

[57] ABSTRACT

The invention includes novel nitro-substituted 1,4-dihydropyridines useful because of their influence on the circulation. Also included in the invention are methods for the preparation of said novel nitro-substituted 1,4-dihydropyridines, compositions containing them and methods for the use of said compounds and compositions.

11 Claims, No Drawings

NITRO-SUBSTITUTED 1,4-DIHYDROPYRIDINES, PROCESSES FOR THEIR PRODUCTION AND THEIR MEDICINAL USE

The present invention relates to certain new nitro-substituted 1,4-dihydropyridines, several process for their preparation and their medicinal use as agents having an influence on the circulation.

It has already been disclosed that 2,6-dimethyl-4-phenyl-1,4-dihydropyridine-3,5-dicarboxylic acid diethyl ester is obtained when benzylideneacetoacetic acid ethyl ester is reacted with β-aminocrotonic acid ethyl ester, or acetoacetic acid ethyl ester and ammonia (Knoevenagel, Ber. dtsch. chem. Ges. 31, 743 (1898)). Furthermore, it is known that certain 1,4-dihydropyridines have interesting pharmacological properties (F. Bossert, W. Vater, Die Naturwissenschaften 58, 578 (1971)).

The present invention relates to new nitrosubstituted 1,4-dihydropyridines of the formula I

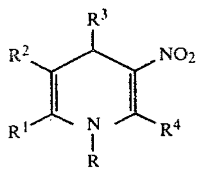

in which

R represents hydrogen, denotes a straight-chain or branched alkyl radical, which is optionally interrupted in the alkyl chain by one or two oxygen atoms, or represents an aryl or aralkyl radical, $R^1$ and $R^4$ independently denote hydrogen, a straight-chain or branched alkyl radical, an aryl radical or an aralkyl or hetero-aryl radical, $R^2$ represents hydrogen or a nitro group, or denotes a group $COR^5$, in which $R^5$ represents an alkyl, aryl or aralkyl radical or a group $OR^6$, in which $R^6$ represents a straight-chain, branched or cyclic, saturated or unsaturated hydrocarbon radical, which is optionally interrupted in the chain by 1 or 2 oxygen or sulphur atoms or in which one hydrogen atom is replaced by a hydroxyl group or by a phenoxy or phenyl group which is optionally substituted by halogen, cyano, amino, alkylamino, alkoxy, alkyl trifluoromethyl or nitro, or by an α-, β-, or γ-pyridyl group, or by an amino group, this amino group optionally carrying either hydrogen and one substituent or two identical or different substituents selected from alkyl, alkoxyalkyl, aryl and aralkyl, and these substituents optionally forming, with the nitrogen atom, a 5-membered to 7-membered ring, which optionally contains, as a further heteroatom, an oxygen, sulphur or nitrogen atom, or $R^6$ represents an aryl group which is optionally substituted by 1 or 2 identical or different substituents selected from alkyl, aryl, aralkyl, alkoxy, halogen, cyano, nitro, trifluoromethyl, trifluoromethoxy, amino and alkylamino, and $R^3$ represents an aryl radical, such as phenyl, biphenyl or naphthyl or a heterocyclic radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, the aryl radical or heterocyclic radical optionally containing 1 to 3 identical or different substituents selected from phenyl, alkyl, alkenyl, alkinyl, alkoxy, alkenoxy, alkinoxy, alkylene, dioxyalkylene, halogen, trifluoromethyl, trifluoromethoxy, hydroxyl, amino, alkylamino, nitro, cyano, azido, carboxyl, carbalkoxy, carboxamido, sulphonamido, $SO_m$-alkyl and $SO_m$-trifluoroalkyl (in which m is 0 to 2).

The compounds of the present invention can also be in the form of their salts or their pharmaceutically acceptable bioprecursors.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the face compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxyethanesulfonic, ethylenesulfonic, benzenesulfonic, halogenbenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds according to the invention display a powerful coronary action and antihypertensive properties.

Furthermore, it has been found that the new nitro-substituted 1,4-dihydropyridines of the general formula I are obtained when (A) an aldehyde of the general formula

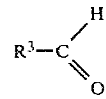

in which $R^3$ has the meaning indicated above, is reacted with an enamine of the general formula

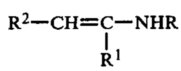

in which R, $R^1$ and $R^2$ have the meanings indicated above, and a nitromethyl ketone of the general formula

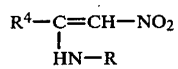

in which $R^4$ has the meaning indicated above, in water or in an inert organic solvent, or (B) an aldehyde of the formula II, as defined above, is reacted with a carbonyl compound of the general formula $R^1$—CO—$CH_2$—$R^2$ V in which $R^1$ and $R^2$ have the meanings indicated above, and a nitroenamine of the general formula

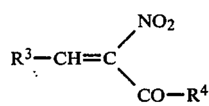

in which R and $R^4$ have the meanings indicated above, in water or in an inert organic solvent, or (C) an enamine of the formula III, as defined above, is reacted with a nitroylidene compound of the general formula

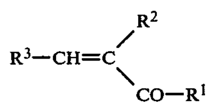

in which $R^3$ and $R^4$ have the meanings indicated above, in water or in an inert organic solvent, or (D) a nitroenamine of the formula VI, as defined above, is reacted with a ylidene ketone of the general formula

R2
R3—CH=C
CO—R1 VIII in which $R^1$, $R^2$ and $R^3$ have the meaning indicated above, in water or in an inert organic solvent.

The new 1,4-dihydropyridine derivatives according to the invention have powerful pharmacological properties. Because of their circulation-influencing action, they can be used as antihypertensive agents, as vasodilators and as coronary therapeutic agents, and are thus to be regarded as an advance in pharmacy.

The synthesis of the compounds according to the invention can be represented by way of example by the following equations, similar reactions occurring with the alternative starting materials.

(A)

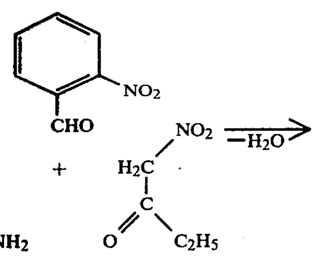

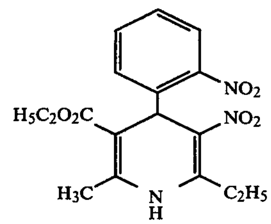

(B)

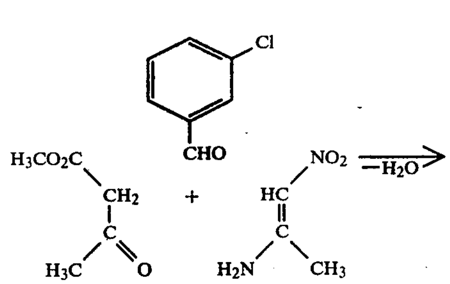

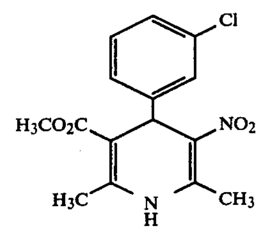

(C)

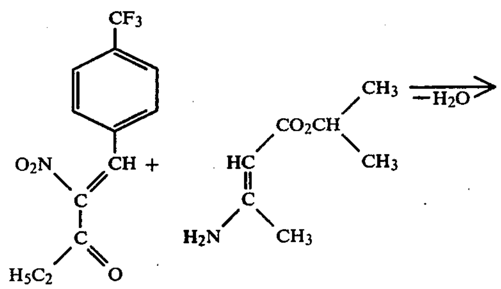

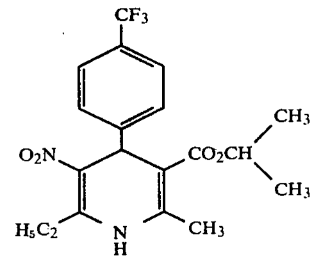

-continued (D)

$$\text{3-cyanophenyl-CH=C(CO}_2\text{-cyclopentyl)(COCH}_3) + \text{HC(NO}_2\text{)=C(CH}_3\text{)NHCH}_3 \xrightarrow{-H_2O}$$

$$\text{cyclopentyl 1,2,6-trimethyl-5-nitro-4-(3-cyanophenyl)-1,4-dihydropyridine-3-carboxylate}$$

Process variant A

According to the procedure indicated under A, an aldehyde of the formula II $$R^3-C(=O)H \quad \text{II}$$

is reacted with an enamine of the formula III $$R^2-CH=C(R^1)-NHR \quad \text{III}$$

and a nitromethyl ketone of the formula IV $$R^4-CO-CH_2-NO_2 \quad \text{IV}$$

In the formula II (as well as in the final product formula I)

$R^3$ preferably represents a phenyl or naphthyl radical, or represents a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical. The heterocyclic radicals mentioned and, in particular, the phenyl radical can contain 1 or 2 identical or different substituents, preferred substituents which may be mentioned being phenyl, straight-chain or branched alkyl with 1 to 8, in particular 1 to 4, carbon atoms, cycloalkyl with 3 to 7 carbon atoms, alkenyl or alkinyl with 2 to 6 carbon atoms, in particular 2 to 3 carbon atoms, alkoxy with preferably 1 to 4, in particular 1 to 2, carbon atoms, alkenoxy and alkinoxy with 2 to 6, in particular 3 to 5, carbon atoms, dioxymethylene, halogen, such as fluorine, chlorine, bromine or iodine, especially fluorine, chlorine or bromine, trifluoromethyl, trifluoromethoxy, nitro, cyano, azido, hydroxyl, dialkylamino with preferably 1 to 4, in particular 1 or 2, carbon atoms per alkyl group, carboxyl, carbalkoxy with preferably 2 to 4, in particular 2 or 3, carbon atoms, carboamido, sulphoamido or $SO_m$-alkyl, m denoting a number from 0 to 2 and alkyl preferably containing 1 to 4, in particular 1 or 2, carbon atoms.

The aldehydes of the formula II used as starting materials are known from the literature or can be prepared by methods which are known from the literature (compare, for example, E. Mosettig, Org. Reactions VIII, 218 et seq. (1954)).

Examples which may be mentioned are: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2-vinylbenzaldehyde, 2-ethinylbenzaldehyde, 2-, 3- or 4-methoxybenzaldehyde, 2-cyclopropylmethoxybenzaldehyde, 2-propargyloxybenzaldehyde, 2-allyloxybenzaldehyde, 2-, 3- or 4-chloro-, -bromo- or -fluorobenzaldehyde, 2-, 3- or 4-trifluoromethylbenzaldehyde, 2-, 3- or 4-trifluoromethoxybenzaldehyde, 4-hydroxybenzaldehyde, 2-, 3- or 4-nitrobenzaldehyde, 2-, 3- or 4-cyanobenzaldehyde, 3-azidobenzaldehyde, 2-, 3- or 4-dimethylaminobenzaldehyde, 3-carbethoxybenzaldehyde, 2-or 4-carbamoylbenzaldehyde, 2-, 3- or 4-methylmercaptobenzaldehyde, 2-, 3- or 4-methylsulphinylbenzaldehyde, 2-, 3- or 4-methylsulphonylbenzaldehyde, 3,4,5-trimethoxybenzaldehyde, 2,4- or 2,6-dichlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-4-trifluoromethylbenzaldehyde and 4-chloro-3-sulphamoylbenzaldehyde; and thiophene-2-aldehyde, furane-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-aldehyde, pyridine-3-aldehyde, pyridine-4-aldehyde, 4-methyl-pyridine-2-aldehyde, 6-methyl-pyridine-2-aldehyde, pyridazine-4-aldehyde, pyrimidine-4-aldehyde, pyrazine-2-aldehyde, quinoline-4-aldehyde, isoquinoline-1-aldehyde, indole-3-aldehyde, benzimidazole-2-aldehyde, quinazoline-2-aldehyde and quinoxaline-2-aldehyde.

In the formula III (as well as in the final product formula I), preferably

R represents a hydrogen atom, or represents a straight-chain or branched alkyl radical with 1 to 8 carbon atoms, in particular 1 to 4 carbon atoms, the alkyl radical optionally being interrupted in the alkyl chain by an oxygen atom, or represents a phenyl radical, or represents an aralkyl radical, in particular a benzyl radical, $R^1$ represents hydrogen, a straight-chain or branched alkyl radical with 1 to 4, in particular 1 to 2, carbon atoms, a phenyl radical or an aralkyl radical, in particular a benzyl radical, and $R^2$ represents hydrogen or a nitro group, or represents the group $COR^5$, wherein $R^5$ represents a straight-chain or branched alkyl radical with 1 to 4 carbon atoms or a phenyl or benzyl radical, or wherein $R^5$ represents the group $OR^6$, wherein $R^6$ represents a straight-chain, branched or cyclic, saturated or unsaturated hydrocarbon radical with up to 8, in particular with up to 6, carbon atoms, which is optionally interrupted in the chain by 1 or 2 oxygen atoms or in which hydrogen is replaced by a hydroxyl group, or by one or more halogen atoms, in particular fluorine, or is replaced by a phenoxy or phenyl group which is optionally substituted by halogen, such as fluorine, chlorine or bromine, cyano, amino, monoalkylamino and dialkylamino with in each case 1 to 2 carbon atoms per alkyl group, alkoxy with 1 to 4 carbon atoms, alkyl with 1 to 4 carbon atoms, trifluoromethyl or nitro, or by an α-, β- or γ-pyridyl group, or by an amino group, this amino group optionally carrying either hydrogen and one substituent or two identical or different substituents from the group comprising alkyl with up to 4 carbon atoms, alkoxyalkyl with up to 4 carbon atoms, phenyl and aralkyl, in particular benzyl, and these substituents optionally forming, with the nitrogen atom, a 5-membered to 7-membered ring, which can contain an oxygen or sulphur atom as a further hetero-atom.

The enaminocarbonyl compounds of the formula III used as starting substances are already known from the literature or can be prepared by methods which are known from the literature (compare A. C. Cope, J. Amer. chem. Soc. 67,1,017 (1945)).

Examples which may be mentioned are: 4-amino-3-penten-2-one, 2-amino-1-nitro-1-propene, 2-methylamino-1-nitro-1-propene, 2-anilino-1-nitro-1-propene, 3-amino-1, 3-diphenylacrolein, β-aminocrotonic acid ethyl ester, β-aminocrotonic acid β-methoxyethyl ester, β-aminocrotonic acid methyl ester, β-aminocrotonic acid butyl ester, β-aminocrotonic acid isopropyl ester, β-aminocrotonic acid cyclopentyl ester, β-methyl-aminocrotonic acid allyl ester, β-ethylaminocrotonic acid propargyl ester, β-amino-β-ethyl-acrylic acid 2-methoxyethyl ester, β-amino-β-benzyl-acrylic acid 2-propoxyethyl ester, β-amino-crotonic acid benzyl ester, β-aminocrotonic acid 2-phenylethyl ester, β-amino-crotonic acid 2-phenoxyethyl ester, β-aminocrotonic acid 4-chlorobenzyl ester, β-aminocrotonic acid 4-nitrobenzyl ester, β-aminocrotonic acid 3,4-dichloro-benzyl ester, β-aminocrotonic acid pyrid-2-ylmethyl ester, β-amino-crotonic acid 2-dimethylaminoethyl ester, β-aminocrotonic acid 2-(N-benzyl-N-methylamino)-ethyl ester, β-aminocrotonic acid 2-(piperidino-1)-ethyl ester and β-aminocrotonic acid 2-(morpholino-4)-ethyl ester.

The nitroenamines listed under formula VI in process variant B are further examples, according to the invention, of enamine compounds of the formula III in which $R^2$ represents a nitro group.

In the formula IV (as well as in the final product formula I), $R^4$ preferably represents hydrogen or a straight-chain or branched hydrocarbon radical with up to 8, in particular up to 6, carbon atoms, which is optionally interrupted in the chain by an oxygen atom or in which hydrogen is replaced by one or more halogen atoms, in particular fluorine, or is replaced by a phenoxy or phenyl group which is substituted by halogen, such as fluorine, chlorine or bromine, cyano, dialkylamino with in each case 1 to 2 carbon atoms per alkyl group, alkyl or alkoxy with 1 to 4 carbon atoms each, trifluoromethyl or nitro, or represents an aryl or hetaryl radical, in particular a phenyl radical, which carries 1 to 3 identical or different substituents from the group comprising halogen, preferably fluorine or chlorine, cyano, alkoxy or alkyl with 1 to 4 carbon atoms per alkyl group, trifluoromethyl or dialkylamino with 1 to 2 carbon atoms per alkyl group, or represents a thienyl, furyl, pyrryl or pyridyl radical.

The nitromethyl ketones of the formula IV used as starting materials are known from the literature in some cases, or they can be prepared by methods which are known from the literature (compare: C. D. Hurd and M. E. Nilson, J. Org. Chem. 20, 927 et seq. (1955); and N. Levy and C. W. Scaife, J. Chem. Soc. (London) 1946, 1103).

Examples which may be mentioned are: nitroacetone, nitromethyl ethyl ketone, nitromethyl n-propyl ketone, nitromethyl i-propyl ketone, nitromethyl n-butyl ketone, nitromethyl i-butyl ketone, nitromethyl n-hexyl ketone, nitromethyl methoxyethyl ketone, nitromethyl trifluoromethyl ketone, nitromethyl benzyl ketone, nitromethyl 3-chlorobenzyl ketone, nitromethyl 2-trifluoromethylbenzyl ketone, nitromethyl 4-nitrobenzyl ketone, nitromethyl 3,4-dichlorobenzyl ketone, nitromethyl β-phenylethyl ketone, ω-nitroacetophenone, 4-methoxy-ω-nitro-acetophenone, phenoxyethyl nitromethyl ketone, ω, 2-dinitroacetophenone, nitromethyl thien-2-yl ketone, nitromethyl fur-2-yl ketone and nitromethyl pyrid-3-yl ketone.

As stated the reaction is carried out in water or an inert organic solvent. The inert organic solvents are preferably, alcohols, such as ethanol, methanol and isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a relatively wide range. In general, the reaction is carried out between 20° C. and 150° C., preferably at the boiling point of the particular solvent.

The reaction can be carried out under normal pressure, but also under increased pressure. In general, it is carried out under normal pressure.

In carrying out the process according to the invention, one mole of aldehyde of the formula II is reacted with one mol of enamine compound of the formula III and one mol of nitromethyl ketone of the formula IV in a suitable solvent. The substances according to the invention are preferably isolated and purified by distilling off the solvent in vacuo and then recrystallising the product, which in some cases is only obtained in the crystalline form after chromatography, from a suitable solvent.

Process variant B

According to the procedure indicated under B, an aldehyde of the formula II

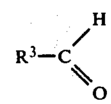

II is reacted with a carbonyl compound of the formula V $$R^1—CO—CH_2—R^2 \qquad V$$

and a nitroenamine of the formula VI

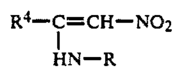

VI

In the formulae II, V and VI, the radicals R, R, $R^2$, $R^3$ and $R^4$ have the meaning indicated under process variant A.

Examples of the aldehydes of the formula II used as starting substances have already been listed under process variant A.

The carbonyl compounds of the formula V which can be used according to the invention are already known or can be prepared by methods which are known from the literature (compare, for example, Houben-Weyl, Methoden der Organischen Chemie (Methods of Organic Chemistry), VII/4, 230 et seq. (1968); and C. D. Hurd and M. E. Nilson, J. Org. Chem. 20, 927 et seq. (1955)).

Examples which may be mentioned are: formylacetic acid ethyl ester, acetoacetic acid methyl ester, n-propionylacetic acid ethyl ester, benzoylacetic acid ethyl ester, acetoacetic acid isopropyl ester, acetoacetic acid cyclopentyl ester, acetoacetic acid allyl ester, acetoacetic acid propargyl ester, acetoacetic acid 2-methoxyethyl ester, acetoacetic acid 2-propoxyethyl ester, acetoacetic acid benzyl ester, acetoacetic acid 2-phenylethyl ester, acetoacetic acid 2-phenoxyethyl ester, acetoacetic acid pyrid-2-yl-methyl ester, acetoacetic acid 2-dimethylaminoethyl ester, acetoacetic acid 2-(N-benzyl-N-methylamino)-ethyl ester, acetoacetic acid 2-(piperidino-1)-ethyl ester, acetoacetic acid 2-(morpholino-4)-ethyl ester, acetylacetone, benzoylacetone and ω-benzoylacetophenone.

The compounds listed under formula IV in process variant A are also examples, according to the invention, of carbonyl compounds of the formula V in the case where $R^2$ is nitro.

The N-substituted nitroenamines of the formula VI used as starting materials are known from the literature in some cases, or they can be prepared by methods which are known from the literature (compare: H. Röhme and K.-H. Weisel, Arch. Pharm. 310, 30–34 (1977)).

The unsubstituted nitroenamines of the formula VI according to the invention (in particular 2-amino-1-nitro-1-propane; melting point: 96°–97° C.) are obtained by heating the ammonium nitronates of the nitromethyl ketones in a suitable solvent, preferably in ethanol.

Examples which may be mentioned are: 2-amino-1-nitro-1-propene, 2-amino-1-nitro-1-butene, 2-amino-1-nitro-1-pentene, 2-amino-3-methyl-1-nitro-1-butene, 2-amino-1-nitro-1-hexene, 2-amino-4-methyl-1-nitro-1-pentene, 2-amino-1-nitro-1-octene, 2-amino-4-methoxy-nitro-1-butene, 2-amino-1-nitro-3,3,3-trifluoro-1-propene, 2-amino-1-nitro-4-phenoxy-1-butene, 2-amino-1-nitro-3-phenyl-1-propene, 2-amino-1-nitro-4-phenyl-1-butene, α-amino-β-nitro-styrene, α-amino-4-methoxy-β-nitro-styrene, 1-amino-2-nitro-1-(thien-2-yl)-ethene, 1-amino-1-(fur-2-yl)-2-nitro-ethene, 1-amino-2-nitro-1-(pyrid-3-yl)-ethene, 2-methylamino-1-nitro-1-propene, 2-anilino-1-nitro-1-propene, 2-ethylamino-1-nitro-1-butene, 2-benzyl-3-methyl-1-nitro-1-butene and 2-methoxy-ethyl-1-nitro-1-pentene.

The reaction is preferably carried out with the same diluents and under the same reaction conditions as under process variant A.

In carrying out the process according to the invention, the substances of the formula II, V and VI participating in the reaction are each employed in equimolar amounts. The compounds according to the invention can be easily purified by recrystallisation from a suitable solvent.

Process variant C

According to process C, an enamine of the formula III

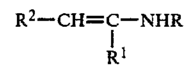

III is reacted with a nitroylidene compound of the formula VII

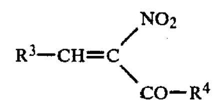

VII

In the formulae III and VII, the radicals R, $R^1$, $R^2$, $R_3$ and $R^4$ have the meaning indicated under process variant A.

Examples of the enamines of the formula III used as starting compounds have already been listed under process variant A.

The nitroylidene compounds of the formula VII which can be used according to the invention are known from the literature in some cases, or they can be prepared by methods which are known from the literature (compare: A. Dornow and W. Sassenberg, Leibigs Ann. Chem. 602, 14 et seq. (1957)).

Examples which may be mentioned are: 1-phenyl-2-nitro-but-1-en-3-one, 1-phenyl-2-nitro-pent-1-en-3-one, 1-phenyl-2-nitro-hept-1-en-3-one, 5-methoxy-2-nitro-1-(3-nitrophenyl)-pent-1-en-3-one,1-(3-chlorophenyl)-2-nitro-4,4,4-trifluoro-but-1-en-3-one, 2-nitro-1-(2-nitrophenyl)-but-1-en-3-one, 2-nitro-1-(3-nitrophenyl)-but-1-en-3-one, 2-nitro-1-(4-nitro-phenyl)-but-1-en-3-one, 2-nitro-1-(2-trifluoromethylyphenyl)-but-1-en-3-one, 2-nitro-1-(4-trifluoromethoxyphenyl)-but-1-en-3-one, 1-(2-cyanophenyl)-2-nitro-pent-1-en-3-one, 1-(2-chlorophenyl)-2-nitro-pent-1-en-3-one, 1-(4-methoxyphenyl)-2-nitro-hex-1-en-3-one, 1-(4-methylphenyl)-2-nitro-non-1-en-3-one, 2-nitro-1-(propargyloxyphenyl)-pent-1-en-3-one, 1-(2-ethinylphenyl)-2-nitro-but-1-en-3-one, 1-(3,4-dichlorophenyl)-2-nitro-but-1-en-3-one, 1-(4-methylmercaptophenyl)-2-nitro-but-1-en-3-one, 1-(4-methylsulphonylphenyl)-2-nitro-but-1-en-3-one, 1-(4-dimethylaminophenyl)-2-nitro-but-1-en-3-one, 2-nitro-1-(thien-2-yl)-but-1-en-3-one, 1-(fur-2-yl)-2-nitro-but-1-en-3-one, 2-nitro-1-(pyrr-2-yl)-but-1-en-3-one, 2-nitro-1-(pyrid-2-yl)-but-1-en-3-one and 2-nitro-1-(pyrid-3-yl)pent-1-en-3-one.

The reaction is preferably carried out with the same diluents and under the same reaction conditions as under process variant A.

In carrying out the process according to the invention, one mol of the nitroylidene compound of the formula VII is reacted with one mol of the enamine compound of the formula III in a suitable solvent. The substances according to the invention are preferably isolated and purified by distilling off the solvent in vacuo and recrystallising the product, which in some cases is only obtained in the crystalline form after chromatography, from a suitable solvent.

Process variant D

According to process D, a nitroenamine of the formula VI

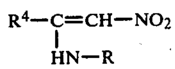

is reacted with an ylidene ketone of the formula VIII

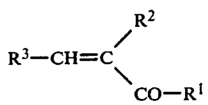

In the formulae VI and VIII, the radicals R, $R^1$, $R^2$, $R^3$ and $R^4$ have the meaning indicated under process variant A.

Examples of the nitroenamines of the formula VI used as starting compounds have already been listed under process variant B.

The ylidene ketones of the formula VIII which can be used according to the invention are known from the literature in some cases, or they can be prepared by methods which are known from the literature (compare: Org. Reactions XV, 204 et seq. (1967)).

Examples which may be mentioned are: benzylidene-acetylacetone, β,β-dibenzoylstyrene, 2'-nitrobenzylidene-acetylacetone, 2'-nitrobenzylideneacetoacetic acid methyl ester, 3'-nitrobenzylideneacetoacetic acid ethyl ester, 2'-trifluoromethylbenzylideneacetoacetic acid n-butyl ester, 2'-cyanobenzylideneacetoacetic acid isopropyl ester, 3'-cyanobenzylideneacetoacetic acid cyclopentyl ester, 2'-methylbenzylideneacetoacetic acid alkyl ester, 2'-methoxy benzylideneacetoacetic acid propargyl ester, 2'-propargyloxybenzylideneacetoacetic acid methyl ester, 2'-cyclopropylmethoxybenzylideneacetoacetic acid methyl ester, 2'-chlorobenzylideneacetoacetic acid 2-methoxyethyl ester, 3'-chlorobenzylideneacetoacetic acid 2-dimethylaminoethyl ester, 2'-bromobenzylideneacetoacetic acid 2-(piperidino-1)-ethyl ester, 2'-fluorobenzylideneacetoacetic acid 2-(N-benzyl-N-methylamino)-ethyl ester, 3'-trifluoromethoxybenzylideneacetoacetic acid propyl ester, 2'-ethinylbenzylideneacetoacetic acid methyl ester, 3'-azidobenzylideneacetoacetic acid ethyl ester, 4'-methoxycarbonylbenzylideneacetoacetic acid n-butyl ester, 3'-methylsulphonylbenzylideneacetoacetic acid isopropyl ester, 3'-methylsulphonylbenzylideneacetoacetic acid cyclohexyl ester, 2'-nitrobenzylideneacetoacetic acid isobutyl ester, 3'-chloro-4'-nitrobenzylideneacetoacetic acid benzyl ester, 4'-chloro-3'-sulphamoylbenzylideneacetoacetic acid 4-chlorobenzyl ester, 3',4'-dichlorobenzylideneacetoacetic acid 4-trifluoromethylbenzyl ester, 3'-cyanobenzylideneacetoacetic acid 2-phenoxyethyl ester, 2'-nitrobenzylideneacetoacetic acid 2-(pyrid-2-yl)-ethyl ester, 3'-nitrobenzylideneacetoacetic acid amide, 2'-trifluoromethylbenzylideneacetoacetic acid dimethylamide, 2'-nitrobenzylidenepropionylacetic acid methyl ester, 2'-cyanobenzylidenepropionylacetic acid ethyl ester, 2'-trifluoromethylbenzylidenebenzoylacetic acid methyl ester, 3'-azidobenzylidene-γ-phenylacetoacetic acid methyl ester, α-acetyl-β-(pyrid-3-yl)-acrylic acid methyl ester, α-acetyl-β-(quinolin-4-yl)-acrylic acid 2-n-propoxyethyl ester, α-acetyl-β-(thien-2-yl)-acrylic acid ethyl ester and α-acetyl-β-(fur-2-yl)-acrylic acid isobutyl ester.

The nitroylidene compounds listed under formula VII in procedure C are further examples, according to the invention, of ylidene ketones of the formula VIII, in which $R^2$ represents a nitro group.

The reaction is preferably carried out with the same diluents and under the same reaction conditions as under process variant A.

In carrying out the process according to the invention, the substances of the formula VI and VII participating in the reaction are each employed in approximately molar amounts.

In the above description of Process variant A, several specific examples are given for the reactants of the formulas II, III and IV. This application is, therefore, to be interpreted to include, as a specific final product, each such product obtained by reaction of any reactant of formula II with any reactant of formula III and any reactant of formula IV. The same interpretation intended with respect to the description of Process variants B, C and D and the specific reactants disclosed for each of said variants.

Depending on the choice of the starting substances, the compounds according to the invention can exist in stereo-isomeric forms, which either behave as mirror images (enantiomers) or do not behave as mirror images (diastereomers).

The present invention relates to both the antipodes and the racemic forms and to the diastereomer mixtures. The racemic forms can be separated into the steroisomerically single constituents in a known manner, as can be diastereomers (compare, for example, E. L. Eliel, Stereochemistry of Carbon Compounds, McGraw Hill, 1962).

Compounds of the formula I according to the invention in which

R represents hydrogen, methyl, phenyl or benzyl, $R^1$ and $R^4$ represents an alkyl radical with 1 to 4, in particular 1 to 2, carbon atoms, or represent a phenyl, benzyl, pyridyl or thienyl radical, $R^2$ represents hydrogen or a nitro group, or represents the group $COR^5$, wherein $R^5$ represents an alkyl radical with, in particular, 1 to 2 carbon atoms, or represents a phenyl or benzyl radical, or $R^5$ represents the group $OR^6$, wherein $R^6$ represents straight-chain, branched or cyclic alkyl, alkenyl or alkinyl with up to 6 carbon atoms, the alkyl and alkenyl group being optionally interrupted by an oxygen atom, and/or the alkyl chain being optionally substituted by phenyl, halogen, such as fluorine or chlorine, phenoxy, halogenophenyl, nitrophenyl, pyridyl, dialkylamino with in each case 1 to 2 carbon atoms in the alkyl radicals or benzylalkylamino with 1 to 3 carbon atoms in the alkyl radical, and $R^3$ represents a phenyl radical, which is optionally substituted by one or two identical or different substituents from the group comprising halogen, nitro, cyano, trifluoromethyl, trifluoromethoxy and alkyl, alkenyl, alkoxy or alkylmercapto with in each case 1 to 4, in particular with 1 to 2, carbon atoms, or represents a naphthyl, pyridyl, thienyl, pyrryl or furyl radical, are of particular interest.

The following active compounds according to the invention may be mentioned, in addition to the preparation examples given below: 1,4-dihydro-2,6-dimethyl-3-nitro-4-phenyl-pyridine, 2-ethyl-1,4-dihydro-6-methyl-3-nitro-4-phenyl-pyridene, 1,4-dihydro-2,6-dimethyl-3-nitro-4-(2-nitrophenyl)-pyridine-5-carboxylic acid methyl ester, 4-(2-chlorophenyl)-1,4-dihydro-2,6-dimethyl-3-nitro-pyridine-5-carboxylic acid ethyl ester, 1,4-dihydro-2,6-dimethyl-4-(4-methoxyphenyl)-3-nitro-pyridine-5-carboxylic acid ethyl ester, 1,4-dihydro-2,6-dimethyl-4-(4-methylphenyl)-3-nitro-pyridine-5-carboxylic acid ethyl ester, 1,4-dihydro-2,6-dimethyl-4-(3-nitrophenyl)-3-nitro-pyridine-5-carboxylic acid n-hexyl ester, 1,4-dihydro-2,6-dimethyl-4-(2-nitrophenyl)-3-nitro-pyridine-5-carboxylic acid t-butyl ester, 4-(3,4-dichlorophenyl)-1,4-dihydro-2,6-dimethyl-3-nitropyridine-5-carboxylic acid i-propyl ester, 4-(2-chloro-5-nitrophenyl)-1,4-dihydro-2,6-dimethyl-3-nitro-pyridine-5-carboxylic acid n-propyl ester, 4-(2-cyanophenyl)-1,4-dihydro-2,6-dimethyl-3-nitro-pyridine-5-carboxylic acid ethyl ester, 4-(3-cyanophenyl)-1,4-dihydro-2,6-dimethyl-3-nitro-pyridine-5-carboxylic acid β-methoxyethyl ester, 1,4-dihydro-2,6-dimethyl-3-nitro-4-(3-trifluoromethoxyphenyl)-pyridine-5-carboxylic acid ethyl ester, 1,4-dihydro-2,6-dimethyl-4-(3-methylmercaptophenyl)-3-nitropyridine-5-carboxylic acid methyl ester, 1,4-dihydro-6-methyl-3-nitro-4-(3-nitrophenyl)-2-trifluoromethyl-pyridine-5-carboxylic acid ethyl ester, 1,4-dihydro-2-methoxyethyl-6-methyl-3-nitro-4-(4-nitrophenyl)-pyridine-5-carboxylic acid methyl ester, 2-benzyl-1,4-dihydro-3-nitro-4-(4-trifluoromethoxyphenyl)-pyridine-5-carboxylic acid β-trifluoroethyl ester, 4-(2-chlorophenyl)-1,4-dihydro-2-n-hexyl-6-methyl-3-nitro-pyridine-5-carboxylic acid benzyl ester, 2,4-di-(2-trifluoromethylphenyl)-1,4-dihydro-6-methyl-3-nitro-pyridine-5-carboxylic acid methyl ester, 1,4-dihydro-6-methyl-3-nitro-4-(3-nitrophenyl)-2-(thien-2-yl)-pyridine-5-carboxylic acid i-propyl ester, 1,4-dihydro-2,6-dimethyl-3,5-dinitro-4-(2-nitrophenyl)-pyridine, 2-ethyl-1,4-dihydro-3,5-dinitro-6-methyl-4-(2-trifluoromethylphenyl)-pyridine, 2-benzyl-1,4-dihydro-3,5-dinitro-6-methyl-4-(pyrid-3-yl)-pyridine, 1,4-dihydro-2,6-dimethyl-3,5-dinitro-4-(pyrr-2-yl)-pyridine, 4-(3-cyanophenyl)-1,4-dihydro-2,6-dimethyl-3,5-dinitro-pyridine and 1,4-dihydro-2,6-di-(β-methoxyethyl)-3,5-dinitro-4-(4-trifluoromethylphenyl)-pyridine.

The new compounds are substances which can be used as medicaments. They have a broad and diverse spectrum or pharmacological action.

In detail, the following main actions could be demonstrated in animal experiments:

(1) On parenteral, oral and perlingual administration the compounds produce a distinct and long-lasting dilation of the coronary vessels. This action on the coronary vessels is intensified by a simultaneous nitrite-like effect of reducing the load on the heart.

They influence or modify the heart metabolism in the sense of saving energy.

(2) The excitability of the stimulus formation and excitation conduction system within the heart is lowered, so that an anti-fibrillation action which can be demonstrated at therapeutic doses results.

(3) The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

(4) The compounds lower the blood pressure of hypertonic animals and can thus be used as antihypertensive agents.

(5) The compounds have strongly muscular-spasmolytic actions which manifest themselves on the smooth muscle of the stomach, the intestinal tract, the urogenital tract and the respiratory system.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes, and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvent, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be only of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following tablets, (including lozenges and grangulates) pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 0.5 to 500 mg, preferably 2.5 to 250 mg, of active ingredient, and for oral administration the daily dose is 2.5 mg to 1 g, preferably 25 mg to 250 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously intravenously), rectally or locally, preferably perorally or parenterally, especially perlingually or intravenously. Preferred pharmaceutical compositions and medicaments are therefore those adapted for oral or parenteral administration, such as tablets and solutions of the active compound using suitable liquid excipients, respectively. Administration in the method of the invention is preferably perorally or parenterally, especially perlingually or intravenously.

In general it has proved advantageous to administer amounts of from 0.01 to 10 mg/kg, preferably 0.05 to 5 mg/kg, of body weight per day in the case of intravenous administration and 0.05 to 20 mg/kg, perferably 0.05 to 5 mg/kg of body weight per day in the case of oral administration to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following examples relate to the preparation of compounds of the present invention.

EXAMPLE 1

1,4-Dihydro-2,6-dimethyl-3-nitro-4-(3-nitrophenyl)-pyridine-5-carboxylic acid methyl ester

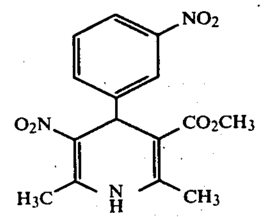

Process variant A 15.1 g (0.1 mol) of 3-nitrobenzaldehyde were heated under reflux together with 11.5 g (0.1 mol) of β-aminocrotonic acid methyl ester and 10.3 g (0.1 mol) of nitroacetone in 150 ml of ethanol for 12 hours. After the reaction mixture has cooled, the solvent was distilled off in vacuo, the oily residue was taken up in a little chloroform and the chloroform solution was chromatographed on a silica gel column (particle size 0.2–0.5 mm) using chloroform, 3% of methanol being added.

The fractions containing the reaction product were concentrated and the residue was taken up in a little isopropanol. The nitrodihydropyridine crystallised in yellow crystals of melting point 204°–206° C.

Yield: 10.3 g (31% of theory).

Process variant D 24.9 g (0.1 mol) of 3-nitrobenzylideneacetoacetic acid methyl ester were heated under reflux together with 10.2 g (0.1 mol) of 2-amino-1-nitro-1-propene in 100 ml of ethanol for 8 hours. After the reaction mixture had cooled, the solvent was distilled off in vacuo and the residue was crystallised from isopropanol; yellow crystals, melting point: 204°–206° C.

Yield: 17.2 g (52% of theory).

EXAMPLE 2

1,4-Dihydro-2, 6-dimethyl-3-nitro-4-(3-nitrophenyl)-pyridine-5-carboxylic acid ethyl ester

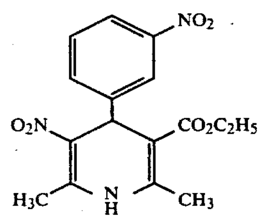

Process variant B 15.1 g (0.1 mol) of 3-nitrobenzaldehyde were heated under reflux together with 13.0 g (0.1 mol) of acetoacetic acid ethyl ester and 10.2 g (0.1 mol) of 2-amino-1-nitro-1-propene in 150 ml of ethanol for 12 hours. After the reaction mixture had cooled, the solvent was distilled off in vacuo, the residue was taken up in a little chloroform and the chloroform solution was discharged onto a silica gel column (particle size 0.2–0.5 mm). The column was eluted with chloroform, 3% of methanol being added.

The fractions containing the reaction product were concentrated and the product was then recrystallised from isopropanol. Yellow prisms of melting point 215° C. were obtained.

Yield: 8.3 g (24% of theory).

EXAMPLE 3

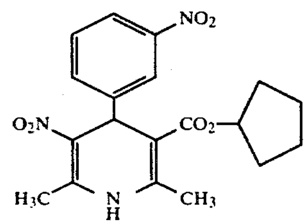

Process variant B 1,4-Dihydro-2, 6-dimethyl-3-nitro-4-(3-nitrophenyl)-pyridine-5-carboxylic acid cyclopentyl ester was obtained analogously to Example 2 by reacting 0.1 mol of 3-nitrobenzaldehyde, 0.1 mol of 2-amino-1-nitro-1-propene and 0.1 mol of acetoacetic acid cyclopentyl ester in ethanol.

Melting point: 174° C. (isopropanol).

Yield: 37% of theory.

Process variant C 23.6 g (0.1 mol) of 2-nitro-1-(3-nitrophenyl)-but-1-en-3-one were heated under reflux together with 16.9 g (0.1 mol) of β-amino-crotonic acid cyclopentyl ester in 150 ml of ethanol for 8 hours. The solvent was then distilled off in vacuo and the residue was crystallised, in yellow crystals of melting point 174° C., from a little isopropanol.

Yield: 18.5 g (48% of theory).

EXAMPLE 4

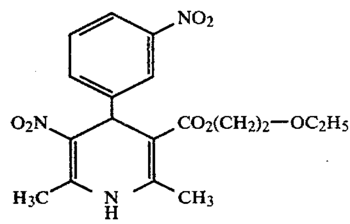

1,4-Dihydro-2,6-dimethyl-3-nitro-4-(3-nitrophenyl)-pyridine-5-carboxylic acid β-ethoxyethyl ester of melting point 140° C. (isopropanol) was obtained analogously to Example 2B by reacting 3-nitrobenzaldehyde with 0.1 mol of acetoacetic acid β-ethoxyethyl ester and 2-amino-1-nitro-1-propene in ethanol. Yield: 36% of theory.

1,4-Dihydro-2,6-dimethyl-3-nitro-4-(3-nitrophenyl)-pyridine-5-carboxylic acid β-ethoxyethyl ester of melting point 140° C. (isopropanol) was obtained analogously to Example 3C by reacting 2-nitro-1-(3-nitrophenyl)-but-1-en-3-one with β-aminocrotonic acid β-ethoxyethyl ester in ethanol.

Yield: 48% of theory.

EXAMPLE 5

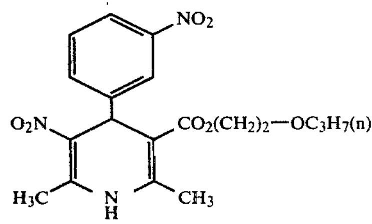

1,4-Dihydro-2,6-dimethyl-3-nitro-4-(3-nitrophenyl)-pyridine-5-carboxylic acid β-n-propoxyethyl ester of melting point 161° (isopropanol) was obtained analogously to Example 2B by reacting 3-nitrobenzaldehyde with 0.1 mol of acetoacetic acid β-n-propoxyethyl ester and 2-amino-1-nitro-1-propene in ethanol.

Yield: 41% of theory.

EXAMPLE 6

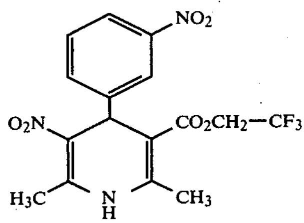

1,4-Dihydro-2,6-dimethyl-3-nitro-4-(3-nitrophenyl)-pyridine-5-carboxylic acid β-trifluoroethyl ester of melting point 196° C. (ethanol) was obtained analogously to Example 1D by reacting 3-nitrobenzylideneacetoacetic acid β-trifluoroethyl ester with 2-amino-1-nitro-1-propene in ethanol.

Yield: 28% of theory.

EXAMPLE 7

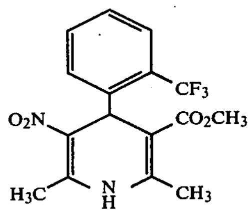

1,4-Dihydro-2,6-dimethyl-3-nitro-4-(2-trifluoromethylphenyl)-pyridine-5-carboxylic acid methyl ester of melting point 176° C. (ethanol) was obtained analogously to Example 1A by reacting 2-trifluoromethylbenzaldehyde with β-aminocrotonic acid methyl ester and nitroacetone in ethanol.

Yield: 36% of theory.

1,4-Dihydro-2,6-dimethyl-3-nitro-4-(2-trifluoromethylphenyl)-pyridine-5-carboxylic acid methyl ester of melting point 176° C. (ethanol) was obtained analogously to Example 1D by reacting 2-trifluoromethylbenzylideneacetoacetic acid methyl ester with 2-amino-1-nitro-1-propene in ethanol.

Yield: 47% of theory.

EXAMPLE 8

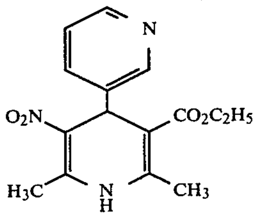

1,4-Dihydro-2,6-dimethyl-3-nitro-4-(pyrid-3-yl)-pyridine-5-carboxylic acid ethyl ester of melting point 264° C. (isopropanol) was obtained analogously to Example 1A by reacting pyridine-3-aldehyde with β-aminocrotonic acid ethyl ester and nitroacetone in ethanol.

Yield: 34% of theory.

EXAMPLE 9

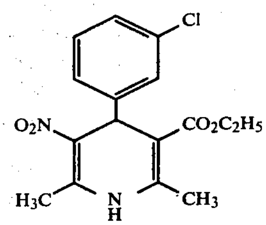

4-(3-Chlorophenyl)-1,4-dihydro-2,6-dimethyl-3-nitro-pyridine-5-carboxylic acid ethyl ester of melting point 168° C. (isopropanol) was obtained analogously to Example 3C by reacting 1-(3-chlorophenyl)-2-nitro-but-1-en-3-one with β-aminocrotonic acid ethyl ester in ethanol.

Yield: 52% of theory.

4-(3-Chlorophenyl)-1,4-dihydro-2,6-dimethyl-3-nitro-pyridine-5-carboxylic acid ethyl ester of melting point 168° C. (isopropanol) was obtained analogously to Example 1D by reacting 3-chlorobenzylideneacetoacetic acid ethyl ester with 2-amin-1-nitro-1-propene in ethanol.

Yield: 48% of theory.

EXAMPLE 10

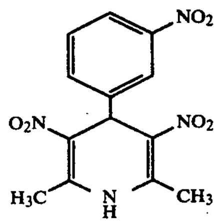

1,4-Dihydro-2,6-dimethyl-3,5-dinitro-4-(3-nitrophenyl)-pyridine of melting point 237°-240° C., with decomposition, (isopropanol) was obtained analogously to Example 1A by reacting 3-nitrobenzaldehyde with nitroacetone and 2-amino-1-nitro-1-propene in ethanol.

Yield: 38% of theory.

1,4-Dihydro-2,6-dimethyl-3,5-dinitro-4-(3-nitrophenyl)-pyridine of melting point 237°-240° C., with decomposition, (isopropanol) was obtained analogously to Example 1D by reacting 2-nitro-1-(3-nitrophenyl)-but-1-en-3-one with 2-amino-1-nitro-1-propene in ethanol.

Yield: 47% of theory.

What is claimed is:

1. A nitro-substituted 1,4-dihydropyridine of the general formula

I

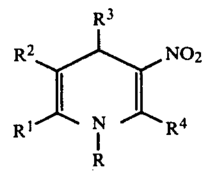

in which

R represents hydrogen, a straight-chain or branched alkyl radical having 1 to 8 carbon atoms, which is optionally interrupted in the alkyl chain by one or two oxygen atoms to form oxa- or dioxa-substituents, or represents a phenyl or benzyl radical $R^1$ and $R^4$ independently denote hydrogen, a straight-chain or branched alkyl radical with 1 to 4 carbon atoms, or a phenyl or benzyl radical, $R^2$ represents hydrogen or a nitro group, or denotes a group $COR^5$, in which $R^5$ represents a $C_1$–$C_4$-alkyl, phenyl or benzyl radical or a group $OR^6$, in which $R^6$ represents a straight-chain, branched or cyclic, saturated or unsaturated hydrocarbon radical with up to 8 carbon atoms, which is optionally interrupted in the chain by 1 or 2 oxygen or sulphur atoms to form oxa-, thia, dioxa- or dithia-substituents or in which one hydrogen atom is replaced by a hydroxyl group or by a phenoxy or phenyl group which is optionally substituted by halogen, cyano, amino, alkylamino or dialkylamino with 1 to 2 carbon atoms per alkyl group, alkoxy with 1 to 4 carbon atoms, alkyl with 1 to 4 carbon atoms, trifluoromethyl or nitro, or by an amino group, this amino group optionally carrying either hydrogen and one substituent or two identical or different substituents selected from alkyl with 1 to 4 carbon atoms, alkoxyalkyl with up to 4 carbon atoms, phenyl and benzyl, or $R^6$ represents a phenyl group which is optionally substituted by 1 or 2 identical or different substituents selected from alkyl with 1 to 4 carbon atoms, phenyl, benzyl, alkoxy with 1 to 4 carbon atoms, halogen, cyano, nitro, trifluoromethyl, trifluoromethoxy, amino and alkylamino with 1 to 4 carbon atoms, and $R^3$ represents a phenyl or naphthyl radical optionally containing 1 or 2 identical or different substituents selected from phenyl, alkyl with 1 to 8 carbon atoms, alkenyl or alkinyl each with 2 to 6 carbon atoms, alkoxy with 1 to 4 carbon atoms, alkenoxy or alkinoxy with 2 to 6 carbon atoms, dioxymethylene, halogen, trifluoromethyl, trifluoromethoxy, hydroxyl, amino, alkylamino with 1 to 4 carbon atoms, nitro, cyano, azido, carboxyl, carbalkoxy with 2 to 4 carbon atoms, carboxamido, sulphonamido, $SO_m$ alkyl with 1 to 4 carbon atoms, and $SO_m$-trifluoroalkyl 2. A compound according to claim 1, in which R represents hydrogen, methyl, phenyl or benzyl, $R^1$ and $R^4$ independently represent an alkyl radical with 1 to 4 carbon atoms, or a phenyl or benzyl, $R^2$ represents hydrogen, a nitro group, or a group $COR^5$, in which $R^5$ represents an alkyl with 1 to 4 carbon atoms, phenyl or benzyl radical, or a group $OR^6$, in which $R^6$ represents a straight-chain, branched or cyclic alkyl, alkenyl or alkinyl with up to 6 carbon atoms, the alkyl and alkenyl group being optionally interrupted by an oxygen atom, and/or the alkyl chain being optionally substituted by phenyl, halogen, phenoxy, halogenophenyl, nitrophenyl, dialkylamino with in each case 1 to 2 carbon atoms in the alkyl radicals or benzylamino with 1 to 3 carbon atoms in the alkyl radical, and $R^3$ represents a phenyl radical, which is optionally substituted by one or two identical or different substituents selected from halogen, nitro, cyano, trifluoromethyl, trifluoromethoxy and alkyl, alkenyl, alkoxy or alkylmercapto with in each case 1 to 4 carbon atoms, or a naphthyl radical.

3. A compound according to claim 2, in which one or more of $R^1$, $R^4$ and $R^5$ represent an alkyl radical with 1 or 2 carbon atoms, the alkyl chain of the alkyl or alkenyl group $R^6$ is substituted by fluorine or chlorine and $R^3$ represents an alkenyl, alkoxy or alkylmercapto group with 1 or 2 carbon atoms.

4. A pharmaceutical composition containing as an active ingredient an effective amount of a compound according to claim 1 in admixture with a solid or liquefied gaseous diluent or in admixture with a liquid diluent other than a solvent of a molecular weight less than 200 except in the presence of a surface-active agent.

5. A pharmaceutical composition of claim 4 in the form of a sterile or isotonic aqueous solution.

6. A composition according to claim 4 or 5 containing from 0.5 to 90% by weight of the said active ingredient.

7. A medicament in dosage unit form comprising an effective amount of a compound according to claim 1 together with an inert pharmaceutical carrier.

8. A medicament of claim 7 in the form of tablets, pills, dragees, capsules, ampoules, or suppositories.

9. A method of combating hypertension and coronary malfunction in warm-blooded animals which comprises administering to the said animals an effective amount of an active compound according to claim 1 either alone or in admixture with a diluent or in the form of a medicament.

10. A method according to claim 9 in which the active compound is administered orally in an amount of 0.05 to 20 mg per kg body weight per day.

11. A method according to claim 9 in which the active compound is administered intravenously in an amount of 0.01 to 10 mg per kg body weight per day.

* * * * *